(12) United States Patent
Kay et al.

(10) Patent No.: US 7,771,457 B2
(45) Date of Patent: Aug. 10, 2010

(54) ORTHOPEDIC PLATE FOR USE IN SMALL BONE REPAIR

(75) Inventors: David B. Kay, Akron, OH (US); Lee A. Strnad, Broadview Hts., OH (US); Dustin Ducharme, Akron, OH (US); G. Martin Wynkoop, Gainsville, FL (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 492 days.

(21) Appl. No.: 11/340,028

(22) Filed: Jan. 26, 2006

(65) Prior Publication Data

US 2006/0173459 A1 Aug. 3, 2006

Related U.S. Application Data

(60) Provisional application No. 60/648,364, filed on Jan. 28, 2005.

(51) Int. Cl.
*A61B 17/80* (2006.01)
*A61F 2/08* (2006.01)
*A61B 17/86* (2006.01)

(52) U.S. Cl. ............... 606/284; 606/280; 606/286; 606/312

(58) Field of Classification Search ............ 606/70, 606/71, 280, 283, 284, 285, 298, 299
See application file for complete search history.

(56) References Cited

U.S. PATENT DOCUMENTS

| | | | |
|---|---|---|---|
| 1,105,105 A * | 7/1914 | Sherman | ............... 606/286 |
| 2,526,959 A | 10/1950 | Lorenzo | |
| 3,716,050 A | 2/1973 | Johnston | |
| 4,867,144 A | 9/1989 | Karas et al. | |
| 4,903,691 A * | 2/1990 | Heinl | ............... 606/70 |

(Continued)

FOREIGN PATENT DOCUMENTS

CH 611147 A5 5/1979

(Continued)

OTHER PUBLICATIONS 6 pages from the Reconstructive Surgery Product Catalog 2005 Integra™ new deals®, New ideas for foot surgery™, including p. 18 Newdeal—Hallu®—Fix.

(Continued)

*Primary Examiner*—Eduardo C Robert
*Assistant Examiner*—Ellen C. Hammond
(74) *Attorney, Agent, or Firm*—Hudak, Shunk & Farine Co. LPA

(57) ABSTRACT

The present invention relates to an orthopedic plate and screw system and instruments for surgical fixation of a small bone or bones. The plate facilitates three dimensional contouring to provide for a variety of applications and to accommodate individual variation in bone shape. The plate has a modified x shape including a central trunk portion including one or more screw holes along a longitudinal axis and a set of divergent upper and an oppositely extending set of divergent lower arms, each arm including screw holes which are placed at a radially equal distance but which diverging asymmetrically from the longitudinal axis relative to its paired upper or lower mate. The screws of the system are self-starting, self-tapping screws including the option of partial or full cannulation.

19 Claims, 6 Drawing Sheets

U.S. PATENT DOCUMENTS

| | | | |
|---|---|---|---|
| 4,959,065 A * | 9/1990 | Arnett et al. | 606/86 B |
| 5,290,281 A * | 3/1994 | Tschakaloff | 606/28 |
| 5,304,180 A | 4/1994 | Slocum | |
| 5,324,290 A | 6/1994 | Zdeblick et al. | |
| 5,459,298 A * | 10/1995 | Tschakaloff | 219/227 |
| 5,607,427 A * | 3/1997 | Tschakaloff | 606/284 |
| 5,681,311 A | 10/1997 | Foley et al. | |
| 5,690,631 A * | 11/1997 | Duncan et al. | 606/281 |
| 5,718,705 A | 2/1998 | Sammarco | |
| 5,749,872 A | 5/1998 | Kyle et al. | |
| 5,779,706 A * | 7/1998 | Tschakaloff | 606/281 |
| 5,827,286 A * | 10/1998 | Incavo et al. | 606/71 |
| 5,853,413 A * | 12/1998 | Carter et al. | 606/281 |
| 6,030,389 A | 2/2000 | Wagner et al. | |
| 6,096,040 A | 8/2000 | Esser | |
| 6,123,709 A * | 9/2000 | Jones | 606/281 |
| D449,692 S | 10/2001 | Michelson | |
| 6,348,052 B1 * | 2/2002 | Sammarco | 606/284 |
| 6,358,250 B1 | 3/2002 | Orbay | |
| 6,454,769 B2 | 9/2002 | Wagner et al. | |
| 6,527,776 B1 | 3/2003 | Michelson | |
| 6,565,570 B2 | 5/2003 | Sterett et al. | |
| 6,565,571 B1 * | 5/2003 | Jackowski et al. | 606/86 B |
| 6,575,975 B2 | 6/2003 | Brace et al. | |
| 6,585,769 B1 | 7/2003 | Muhanna et al. | |
| 6,652,530 B2 * | 11/2003 | Ip et al. | 606/284 |
| D520,637 S | 5/2006 | Kay et al. | |
| 7,052,499 B2 * | 5/2006 | Steger et al. | 606/291 |
| 7,108,697 B2 * | 9/2006 | Mingozzi et al. | 606/297 |
| 7,128,744 B2 | 10/2006 | Weaver et al. | |
| 7,166,111 B2 * | 1/2007 | Kolb et al. | 606/96 |
| 7,288,095 B2 * | 10/2007 | Baynham et al. | 606/288 |
| 7,335,204 B2 * | 2/2008 | Tornier | 606/284 |
| 7,438,715 B2 * | 10/2008 | Doubler et al. | 606/71 |
| 2003/0199875 A1 | 10/2003 | Mingozzi et al. | |
| 2004/0193163 A1 | 9/2004 | Orbay | |
| 2005/0015089 A1 | 1/2005 | Young et al. | |
| 2005/0192577 A1 * | 9/2005 | Mosca et al. | 606/69 |
| 2006/0106387 A1 * | 5/2006 | Fanger et al. | 606/69 |
| 2006/0122607 A1 * | 6/2006 | Kolb | 606/71 |
| 2006/0129151 A1 | 6/2006 | Allen et al. | |
| 2006/0173458 A1 | 8/2006 | Forstein et al. | |
| 2006/0173459 A1 | 8/2006 | Kay et al. | |
| 2006/0200145 A1 | 9/2006 | Kay et al. | |
| 2006/0229610 A1 * | 10/2006 | Piehl | 606/61 |
| 2007/0073298 A1 | 3/2007 | Beutter et al. | |
| 2007/0173840 A1 * | 7/2007 | Huebner | 606/69 |
| 2007/0185493 A1 | 8/2007 | Feibel et al. | |
| 2008/0300632 A1 | 12/2008 | Butler et al. | |
| 2008/0300637 A1 | 12/2008 | Austin et al. | |

FOREIGN PATENT DOCUMENTS

| | | | |
|---|---|---|---|
| DE | 203 09 361 U1 | | 5/1979 |
| EP | 1 468 655 A2 | | 10/2004 |
| FR | 2 233 973 A1 | | 2/1975 |
| FR | 2 405 706 | * | 10/1977 |
| FR | 2 405 062 A1 | | 6/1979 |
| FR | 2 405 705 A1 | | 6/1979 |
| FR | 2 405 706 A1 | | 6/1979 |
| JP | 11299804 | | 11/1992 |
| WO | WO 02/096309 A1 | | 12/2002 |
| WO | WO 2004086990 A1 | * | 10/2004 |

OTHER PUBLICATIONS

TOM™-Platte by DARCO® Innovation in Foot Care Technology, Dec. 8, 2006 (2 pages).
New Trauma Products from AO Development, Jun. 2006 (p. 6).
4 pages from the INTEGRA™ Jan. 2005 new deal®, Hallu® -S Plate.
Locking Clavicle Plate System by ACUMED® Jul. 2005, (7 pages).
3.5 mm LCP Superior Anterior Clavicle Plates, by SYNTHES® Sep. 2008 (24 pages).
PERI-LOC Locked Plating System—Clavicle Locking Plate by Smith&Nephew, May 2007 (16 pages).
Locking Bone Plate System for Hallux-Valgus Corrections "Opening or Closing Base Wedge" Osteotomy by MetaFix™ Feb. 2005 (2 pages).

* cited by examiner

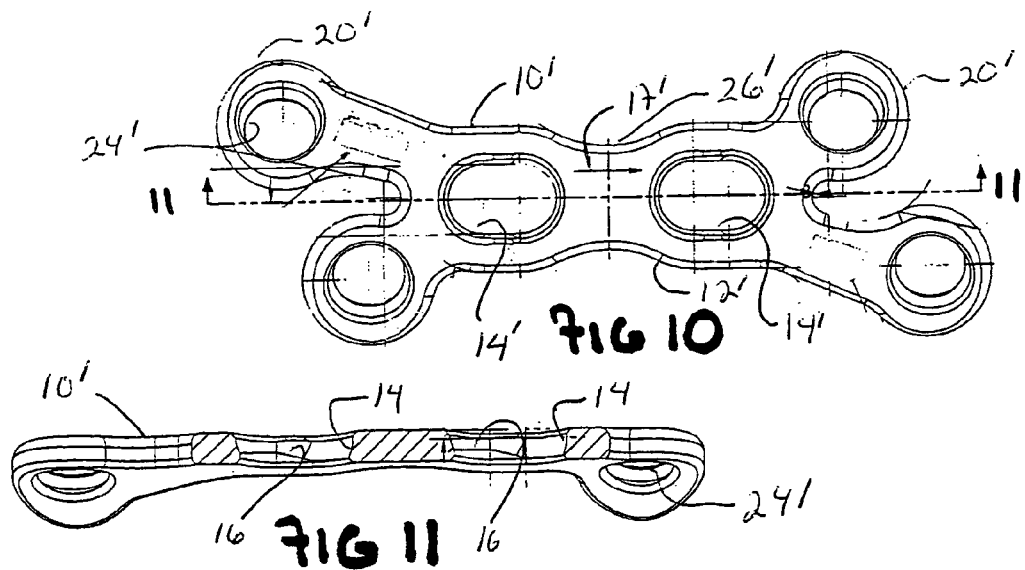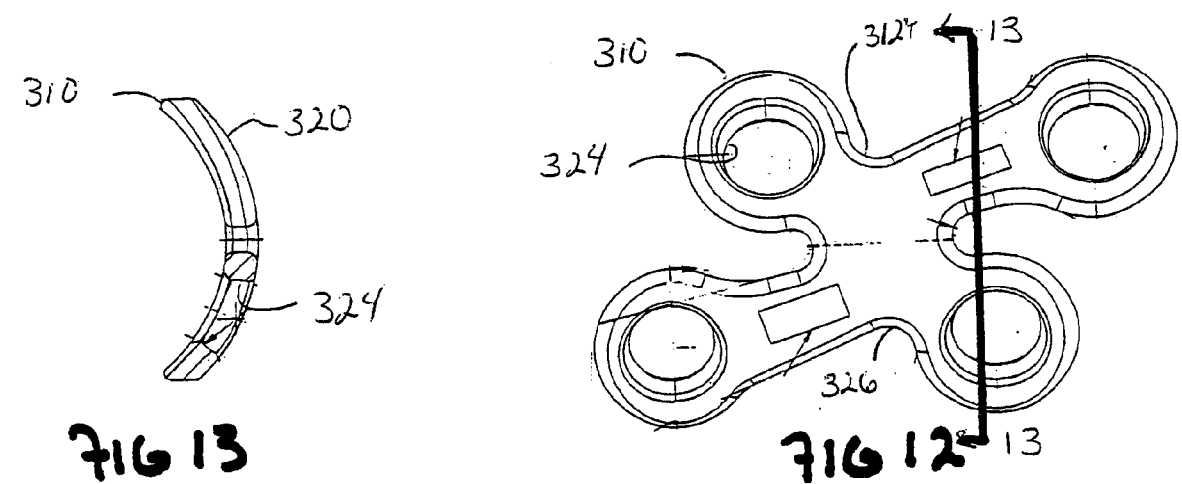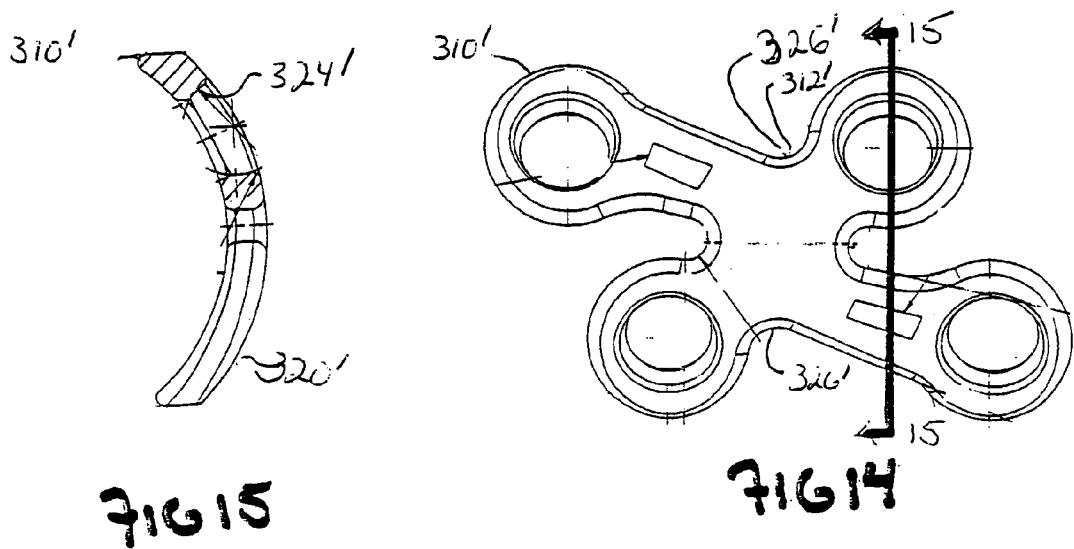

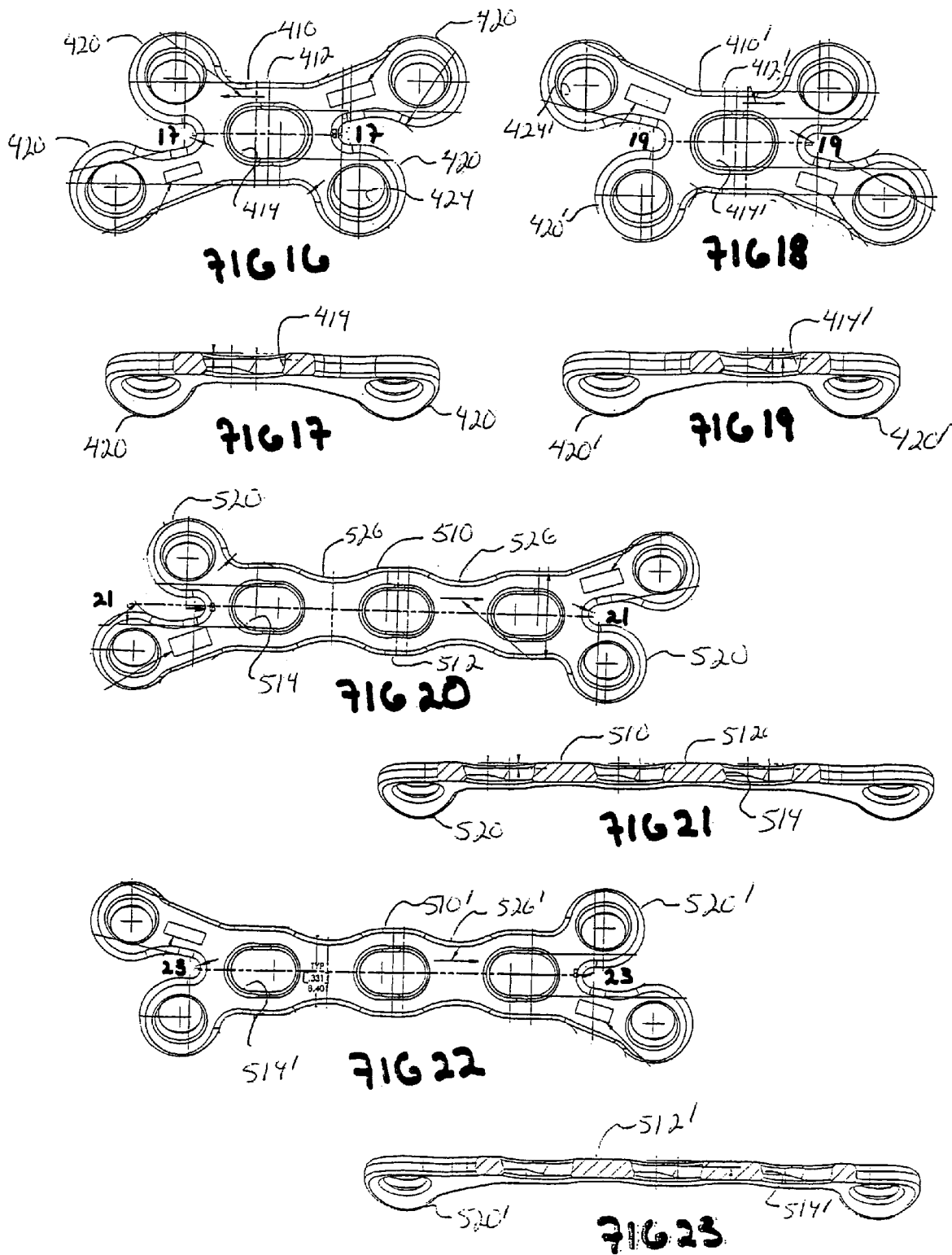

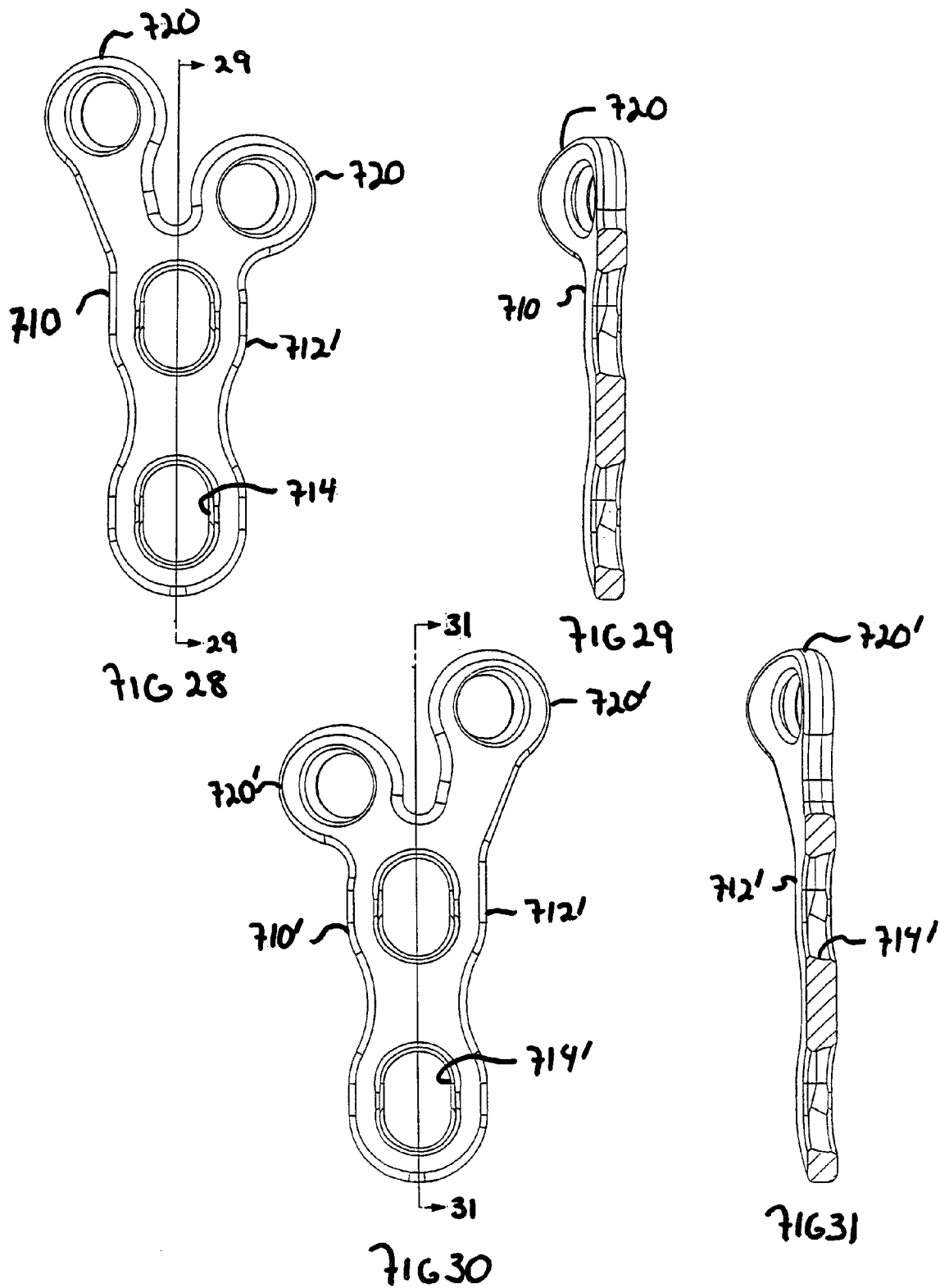

ORTHOPEDIC PLATE FOR USE IN SMALL BONE REPAIR

CROSS-REFERENCE

This application claims the benefit of priority under 35 U.S.C. §119 of U.S. Provisional Application Ser. No. 60/648,364 filed on Jan. 28, 2005.

The present invention relates to an orthopedic plate in particular for surgical repair or reconstruction of a small bone and to a system of orthopedic plates which are presented during surgery for use for a variety of indications.

BACKGROUND OF THE INVENTION

The field of orthopedic medicine has grown tremendously in the past fifty years as surgical techniques, implants and instrumentation have developed and been improved. The medical companies have tended to focus their attention on the largest market areas so that some areas of the body, such as the spine, knees and hips, have received intense focus from the large medical companies. While the small bones are frequently subject to the need for re-constructive surgery for example, as a result of trauma, to counteract the effects of aging or to repair congenital deformities, this area has typically not received the same degree of attention from the medical companies as joint replacement, trauma and spinal areas. Consequently, the products available to the small bone surgeon often represent scaled down versions of products designed for the large long bone market which are not adequate for the fine bones and delicate procedures required of the small bone surgeon. Additionally, while there is a wide variety in the exact shape and mass of all bones, these variations become more problematic in providing orthopedic implants for small bone applications since there is less room on and about the bone for the surgeon to place and fix the construct. These bones are finer and have less surface area for placement of an implant, and less mass for the placement of screws and as a result, individual variations become more problematic for implants of stock design.

One problem that needs to be avoided in the delicate environment of the small bone area is the interference of screws, with other screws, and with the function of ligaments and tendons. While it may be desirable to design an orthopedic plate so that securing screws converge in order to cause compression or increase the pullout strength, it is difficult when a screw impinges on or conflicts with the desired placement of another screw. Some surgeons prefer bicortical fixation in which a screw is sized so that the distal end is secured in cortical bone giving the screw better purchase, however, other surgeons may prefer to avoid placing a screw so that it projects beyond the outer surface of the anchoring bone. These factors are complicated by the relative lack of soft tissue and the presence of ligaments and tendons in the small bone areas. Consequently, the less forgiving biological environment in which the small bone surgeon works requires greater procedural precision and calls for specialized implants and tools.

The present invention is designed to meet the specific needs of the small bone surgeon to facilitate effective and repeatable procedures which provide for ease of use and a range of function for this specific area of specialization. The present invention is specifically intended to provide for the treatment of a broad range of indications including relatively straightforward fracture repair following trauma in an otherwise healthy individual where plates are used to maintain the integrity of the bones while they heal, as well as for more complex surgeries such as reconstruction to correct congenital or age related deformation. Reconstruction often includes arthrodesis or partial or total fusion which involves removal of a joint and the use of a mechanical-biological construct to keep the bones immobile while fusion occurs. Further small bone surgeons may be called upon to achieve soft-tissue balancing by readjusting the length of tendons and ligaments or to reshape the bone itself through removal or repositioning in a procedure known as an "osteotomy". In an aging or diabetic population, these procedures may also involve dealing with the difficulties of poor quality bone and/or compromised soft tissue.

These surgeons typically include sub-specialists such as hand surgeons and foot and ankle orthopedic surgeons and podiatric surgeons, but can also include general orthopedic surgeons who may be called upon to perform procedures on the small bones.

The present invention provides a plate with bilaterally asymmetrical (meaning that the left half of the plate is not exactly the same as the right half of plate taken from the medial axis) and bi-planar screw fixation (meaning that the screws do not lie in a single plane) and further designed to facilitate three dimensional contouring to provide for a variety of applications and to accommodate individual variation in bone shape. The plate is designed specifically for the small bone market, i.e. for use in bones distal to the clavicle, elbow and knee, including, for example, the ulna, radius, tibia, fibula, as well as the metacarpals, carpals, metatarsals, tarsals, and phalanges. The plate can be used in applications previously mentioned, for example those that require fixation to a single bone such as the stabilization of a fracture or the plate can be used across two or more bones so as to facilitate total or partial fusion. The plate is configured to bend laterally, longitudinally, and to wrap or spiral about its longitudinal axis so that it can be molded to an optimal shape for small bone procedures. The plate is designed to provide optimal stabilization of fractures and osteotomies by providing multi-planar fixation that allows for better pull-out and limited axial loading to the bone. The plate is further designed to accelerate fusion success by reducing or eliminating torsional or twisting stresses to the bone segments during the healing process. In addition, when desired, the plate can be shaped so as to apply a compressive, or even a tensile, force, for example, along the longitudinal axis of a bone.

Further while the plate exhibits a bilateral asymmetry (meaning that the left half is not the same as the right half), it exhibits a transverse mirror symmetry (meaning that one end of the plate is a mirror image of the other end of the plate relative to a mid-plane which is perpendicular to the longitudinal or medial axis). Thus, the plates display a handedness, or are presented in an alpha and beta version that are like enantiomorphs of each other in so far as they are mirror images but are not identical. This allows the plates to be presented for example in a surgical tray as a system of plates. The system includes one or more alpha and beta version where individual versions of the alpha and beta plates can vary in the length of the central trunk portion and the number of screw holes in the trunk. This allows the surgeon to select his plate during surgery after opening the wound area and considering the plating needs.

The plate has a central trunk portion including one or more screw holes separated by a waist shaped linking portion along a longitudinal axis and a set of upper and lower arms including screw holes which are placed at an equal distance from the longitudinal axis but which diverge asymmetrically from the longitudinal axis to avoid conflicts in the screw placement of the paired arm, specifically, so that the screws of a set of arms avoid impinging on each other. The plate is radiused about the inferior surface, (i.e. the surface which faces toward and which may, but does not have to fully contact the bone), with a curvature corresponding generally to the curvature of a bony surface. The upper pair of arms, and the lower pair of arms continue this curvature and the through holes are placed so that the angle of the longitudinal axis of the screws converge in the direction of the distal end of the screw. The screw holes are placed with the longitudinal axis perpendicular to a tangent to the top surface of the arm with the effect that the longitudinal axes of the screws converge in the direction of the distal end. The convergence of the screw holes increases the pull-out strength of the screws.

Further the screw holes are rounded and the corresponding mating heads of the screws are rounded and have a low profile so that the screws can be seated with their longitudinal axes at a variety of angles. Preferably, there is at least 20° of conical rotation, and more preferably 25°, and most preferably 30° of conical rotation of the screw axis in relation to the longitudinal axis of the screw hole (i.e. the longitudinal axis of the screw can be rotated through a conical shape about the axis of the screw hole where the apex of the cone describes an angle of 30°).

While the screws are at convergent angles, the screws typically do not in fact impinge on each other, or conflict in their placement since each of the arms of the plate in a pair form a different angle to the central trunk so that the longitudinal axis of the screws are offset from each other along the length of the plate. The radiused configuration of the plate is designed to increase operating room efficiency by facilitating commonly desirable shapes while maintaining the required strength and by permitting bending without deforming the screw holes. This results in making customization in anticipation or during surgery easier.

The screws useful with the plate of the present invention are self-starting, self-tapping screws including the option of partial or full cannulation. The screws include a unique cutting end having multiple flutes, and preferably 2 or 3 flutes about a conical recess. The screws further include a partial taper of the inner diameter in the proximal end over the first several thread turns, for example over 2-8, and preferably over 3-5 turns in order to increase the fatigue life of the screw as well as providing potential physiological advantages in use. The screws further include a torque driving recess that may be a hexagon, a torx shape, or a modification of a torx shape, i.e. a multilobe shape having from 3 to 12 lobes, and preferably having 4 to 8 rounded recesses or lobes. The recess can be of a constant size in the direction of the longitudinal axis, or can taper inward along the longitudinal axis of the screw toward the bottom of the recess. The screws have a low profile, head which is rounded at the junction of the head and the shaft, and also rounded from the maximum diameter toward the top surface or the proximal end relative to the insertion tip, which includes the torque driving recess. This rounded low profile head keeps the screw from having any sharp projecting edges which could provide an irritation to the tissue in the vicinity of the plate and further seats in the plate so that no more than 10% by volume of the screw head projects from the plate.

The instruments for use with the system are well-balanced and ergonomically designed with sufficiently long handles to place the surgeon's hands outside of the line of radiation and designed to reduce fatigue in the operating room.

The plate system of the present invention is thus designed to fit a range of needs of the surgeon operating on the small bones to allow him or her to perfect a variety of techniques using a set of instruments and a customizable plate and screw construct.

BRIEF DESCRIPTION OF THE DRAWINGS

FIG. 10 is a top view of a beta version of the first embodiment of a plate in accordance with the invention;

FIG. 11 is a cross section of the plate of FIG. 10 taken along line 11-11;

FIG. 12 is a top view of an alpha version of a third embodiment of a plate in accordance with the invention;

FIG. 13 is a cross section of the plate of FIG. 12 taken along line 13-13;

FIG. 14 is a top view of a beta version of the third embodiment of a plate in accordance with the invention;

FIG. 15 is a cross section of the plate of FIG. 14 taken along line 15-15;

FIG. 16 is a top view of an alpha version of a fourth embodiment of a plate in accordance with the invention;

FIG. 17 is a cross section of the plate of FIG. 16 taken along line 17-17;

FIG. 18 is a top view of the beta version of the fourth embodiment of the plate in accordance with the invention;

FIG. 19 is a cross section of the plate of FIG. 18 taken along line 19-19;

FIG. 20 is a top view of an alpha version of a fifth embodiment of a plate in accordance with the invention;

FIG. 21 is a cross section of the plate of FIG. 20 taken along line 21-21;

FIG. 22 is a top view of the beta version of the fifth embodiment of the plate in accordance with the invention;

FIG. 23 is a cross section of the plate of FIG. 22 taken along line 23-23;

FIG. 28 is a top view of an alpha version of a seventh embodiment of a plate in accordance with the invention;

FIG. 29 is a cross section of the plate of FIG. 28 taken along line 29-29;

FIG. 30 is a top view of the beta version of the seventh embodiment of the plate in accordance with the invention; and FIG. 31 is a cross section of the plate of FIG. 30 taken along line 31-31.

DETAILED DESCRIPTION OF THE INVENTION

Figure 1:
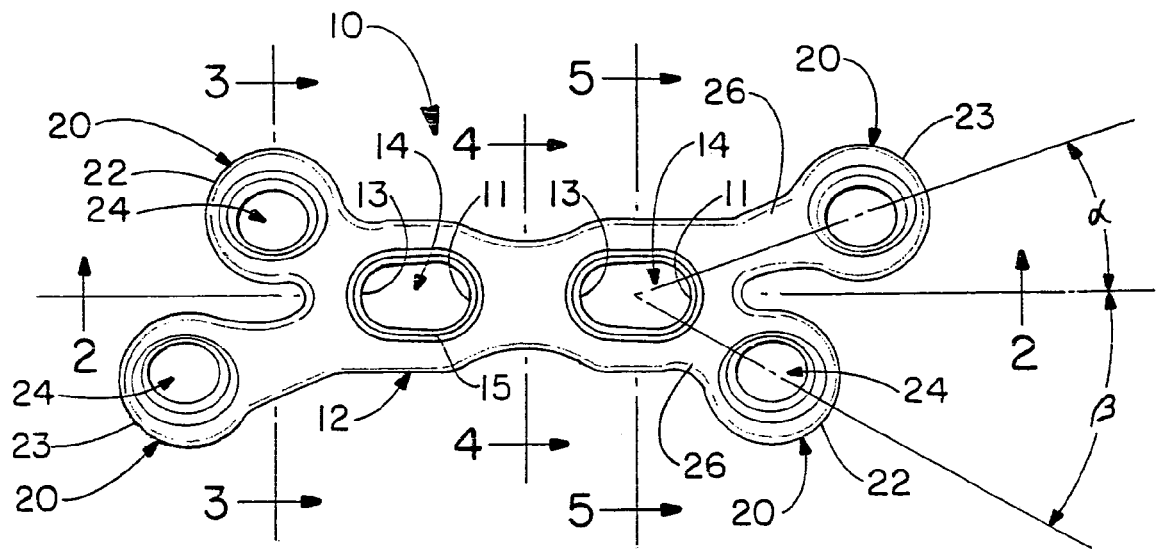
FIG. 1 is a top view of an alpha version of a first embodiment of an orthopedic plate in accordance with the invention.
Figure 2:
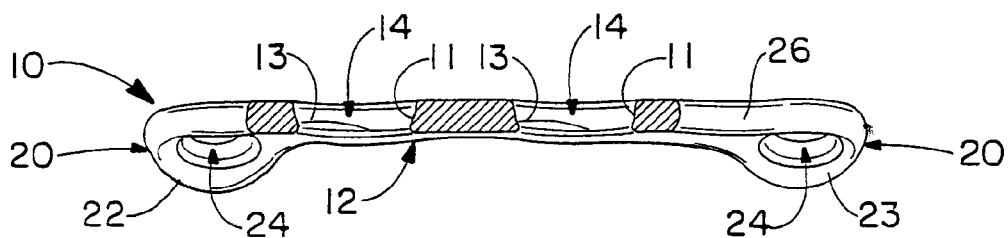
FIG. 2 is a cross-section of the plate of FIG. 1 taken along line 2-2.

The plate 10 of the present invention is shown having a bilaterally asymmetric shape which can be thought of as being similar to the Greek letter X with foreshortened opposing diagonal legs extending from a central trunk portion 12 defining the longitudinal axis of the plate. As shown the trunk portion 12 includes two screw holes or slots 14 along the longitudinal axis. However, as can be seen from FIGS. 9 through 31 the plate can be presented in a version which has no slots or screw hole, or a plurality of screw holes, up to 8 or more. The number of screw holes in the trunk portion 12 will depend on the length of the plate, and may range from 0 to 8, and more preferably from 2 to 4. In one embodiment these holes are compression holes. The screw holes 14 are preferably slotted or elongated and optionally may have a larger radius area 11 on each of the screw holes facing in the same direction, and a smaller radius area 13 in order to induce a compression toward the smaller radius end. The holes may also or alternatively have a shallow shoulder or lip 16 which descends toward the inferior surface of the plate to allow the plate to be set initially and subsequently to be slide into a different position as the screws are tightened down. This allows compression to be applied across the middle of the trunk section. The plates include a visual indicator of the direction of the compression, such as an arrow 17. Further, the screw holes include annular rings 15 of increased thickness in the vertical direction about through holes 14.

The through holes 14 in the trunk portion 12 have a longitudinal axis that is perpendicular to a plane tangent to the top radius of the plate. The area linking the screw holes has a decreased width so as to define a waist area 26 that will bend laterally (or "curve") relative to the longitudinal axis and which will bend longitudinally to form a curved area in and out of the plane of the plate. This thinner area also facilitates twisting of the plate so as to allow the plate to spiral, or wrap around it longitudinal axis. The increased annular area around the through bores resists deformation when a bending device is used to apply a force to the plate through the screw holes.

The plate 10 also includes at least one set, and preferably two opposing sets of arms 20. As viewed in FIG. 1, these sets of arms can be viewed as a set of diagonally opposed short 22 and long arms 23, or as a pair or upper and lower arms which are mirror images, although it is understood that the orientation of the plate can vary even after the plate has been fixed to the bone so that the terms upper and lower are only used to distinguish the pair on one side of the trunk portion 12 from the pair on the other side of the trunk portion 12. Each of the arms in a set includes screw holes 24 which are placed at a radially equal distance but which diverging asymmetrically from the longitudinal axis of the plate 10. More specifically as viewed from the top each set of arms includes one arm that defines a smaller angle of divergence a from the longitudinal axis of the trunk portion than the angle of divergence of the other arm β. For example, the first angle shown in FIG. 1 at a may be from about 5° to about to 25°, and more preferably from about 10° to about to 20° and most preferably from about 12° to about to 16°, while the second angle shown at β from about 10° to about to 35°, and more preferably from about 15° to about to 30° and most preferably from about 22° to about to 26° with a preferred difference in the angles beings from about 2° to about to 20°, and more preferably from about 4° to about to 16° and most preferably from about 8° to about to 12°.

In addition to the angled arms of this asymmetrical dog-bone shape facilitating a variety of useful positions in the small bone area, the plate of the present invention is sized to fie the needs of the small bone specialist. For small bone usage, the total length of the plate along its longitudinal axis is from about 25 mm to about 80 mm, depending on the number of screw holes in the trunk portion. The total width is from about 12 mm to about 18 mm, width an inferior radius of curvature of about 8 mm to about 12 mm and a concentric radius on the superior side. Typically, the waist area measures from about 7.5 mm to about 10 mm from the center of the larger, i.e. about 3.8 mm, radiused portion of the holes. The trunk portion has a width of about 7 mm to about 9 mm wide at the wider parts and about 3 mm to about 5 mm wide at the narrower waist portion. The longer arm has a length along the longitudinal axis of the plate from the center of the screw hole to the center of the plate for a two-hole trunk of from about 12 mm to about 16 mm, with a width of about 3 mm to about 5 mm. The shorter arm has a comparable length of from about 7 mm to about 15 mm with a narrowed width of about 2.5 to about 5 mm. In a further embodiment the plate could be modified for use in the long bones with a length of up to about 400 mm with a width of up to about 50 mm, and proportional sizes for the arms and thickness.

On the inferior side, or the side that would be facing (which contemplates opposing or touching or partially touching the) bone surface in use, the arms continue the radius of curvature of the trunk portion. The superior or top side of the plate has a similar radius of curvature as the top surface of the plate and has an outline that corresponds with the shape of the bottom of the plate (excluding the optional thickened annular area surrounding the screw holes which would act to shield these holes against deformation during bending.) The screw holes also include a rounded concavity to mate with the rounded shape of the head of the screw to allow of variable axis positioning. The screw holes 24 are placed with the longitudinal axis perpendicular a tangent to the top surface of the arm with the effect that the longitudinal axes of the screws converge in the direction of the distal end. This increases the pull-out strength of the plate/screw construct. Since the arms are asymmetrical relative to each other, and in particular since they diverge from the longitudinal axis of the trunk portion at differing angles, conflicts in the positions of paired screws is avoided so that the screws of a set of arms typically do not impinge on each other. This is even more important in instances where the plate is bent around the longitudinal axis so as to wrap around the longitudinal axis of the bone.

The arms 20 also each include a screw hole 24 which, like the trunk portion 12 has a linking portion 26 that joins the screw hole to the trunk portion. Again this design facilitates the desired bending while resisting deformation of the screw holes 24 when they are used with the bending instrument to contour the plate. While the angle of the arms 20 of each one of a pair of a respective set of arms (both top and bottom and right and left pairs) varies so as to create a bilateral asymmetry, meaning that the plate is not symmetrical with respect to a plane that passes through the longitudinal axis in the vertical direction from the superior (the top side relative to the bone) to the inferior side (the side facing the bone), the "first plane". However, the position of the arms in each set is preferably flipped so that the symmetry of the plate shape about a plane transverse to the first plane is a mirror image, this is defined herein as transverse mirror symmetry. Thus, the arms can be considered as congruent diagonally opposing pairs 22, 23. Since the plates in come two version, an alpha version and a beta version, the difference between these two version is that the relative positions of the diagonal pair is switched, making the alpha version a mirror image of the beta version.

Figure 3:
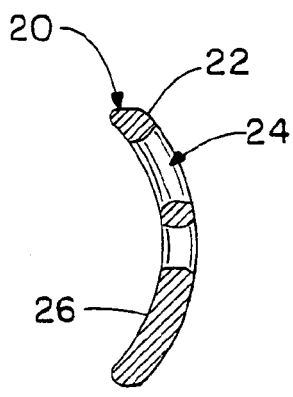
FIG. 3 is a cross-section of the plate of FIG. 1 taken along line 3-3.
Figure 4:
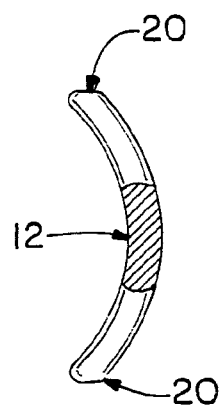
FIG. 4 is a cross-section of the plate of FIG. 1 taken along line 4-4.
Figure 5:
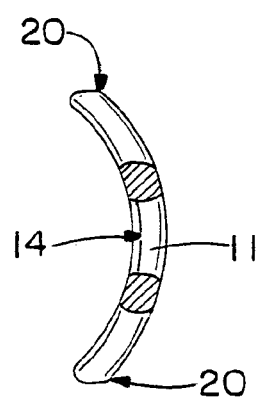
FIG. 5 is a cross section of the plate of FIG. 1 taken along line 5-5.

The screws holes of the trunk portion can include means to induce a compressive force in one direction, such as a ramped area on each screw hole. These ramped areas would be ramped on the same side of the holes looking down from the top of the plate. Typically the first screw implanted stabilizes and the second screw is used to achieve compression. Further the length of each of the arms of a pair will vary so that the radial length of the center of the screw hole to the intersection with the longitudinal axis will be the same. As shown in FIGS. 3-5, the plate includes a radial curve about the longitudinal axis. The radius is typically about 10 mm with a transverse dimension from the edge of one arm to the edge of the other arm of an upper or lower pair being about 15 or 16 mm for typical small bone usage, and the screw bore having a longitudinal axis of about 24° to an plane passing through the longitudinal axis of the plate. The bores are typically about 3.75 mm for a 3.5 mm diameter screw for small bones excluding the smallest of applications which would include phalanges. Again, for the smallest application as well as long bone embodiments the screws and corresponding screw holes could be sized to range from a 1.5 mm diameter screw up to a 7.5 mm diameter screw. In a further embodiment, the bore could be threaded.

Figure 6:
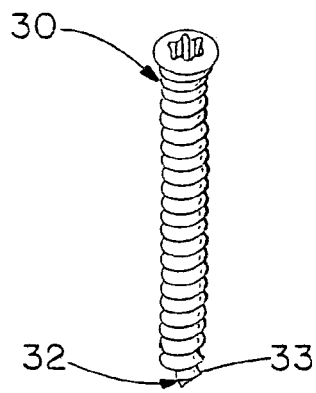
FIG. 6 is a perspective view of a screw used with the present system.
Figure 7:
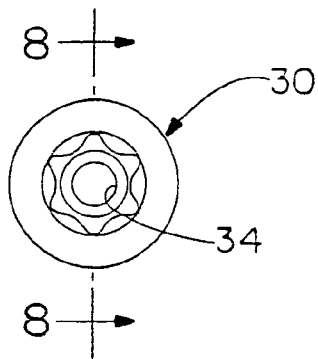
FIG. 7 is a detail of the torque receiving recess of the screw shown in FIG. 6.
Figure 8:
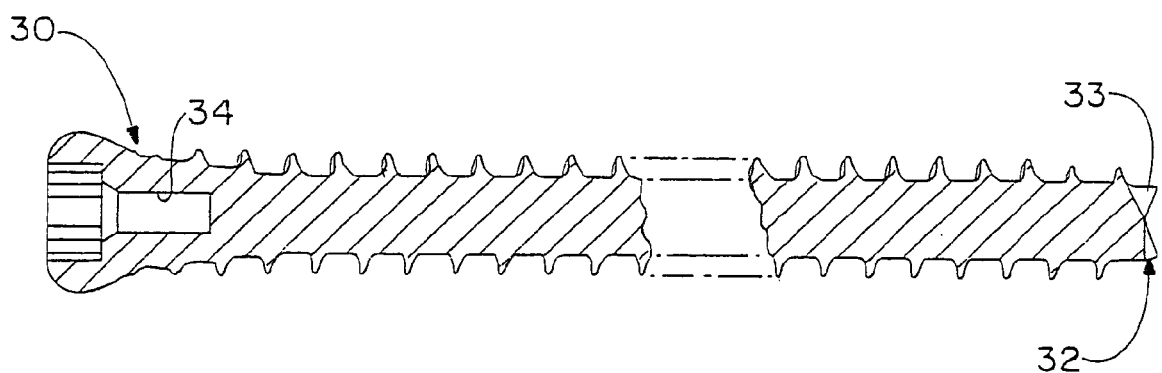
FIG. 8 is a cross-section of the screw of FIG. 6 taken along line 6-6.

FIG. 6 shows a screw 30 used with the plate system of the present invention. The distal end of the screw includes a cutting tip 32 which is self-starting and self-tapping. This aspect is defined by a conical recess and a plurality of flutes 33. These screws 30 can optionally include partial or full cannulation 34. The head of the screw is spherical and includes a torque driving recess 36, such as a modified multilobe shape as is shown in FIG. 7. The screw has a cancelleous thread 38 with a constant major diameter 40 and a minor diameter 42 that tapers proximally in order to increase fatigue life of the screw and to improve compression and compensate for bone resorption.

Figure 9:
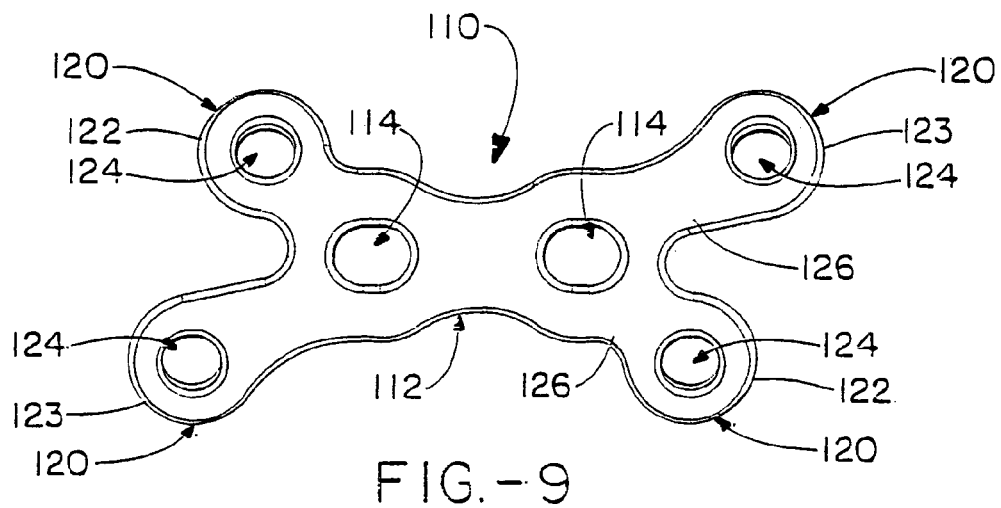
FIG. 9 is a top view of an alpha version of a second embodiment of a plate in accordance with the invention.
Figure 24:
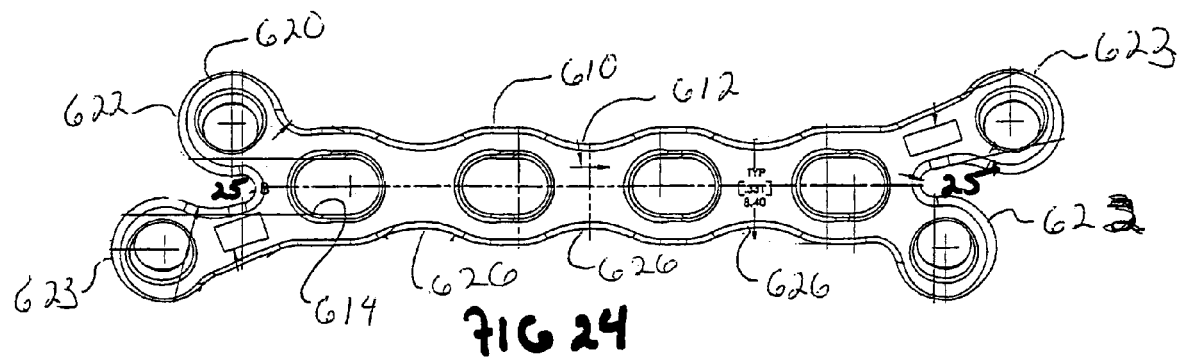
FIG. 24 is a top view of an alpha version of a sixth embodiment of a plate in accordance with the invention.
Figure 25:
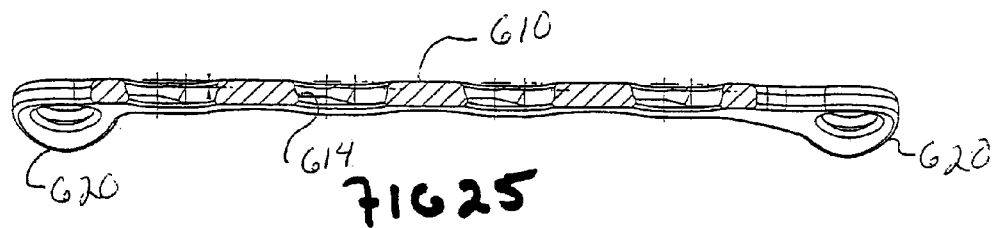
FIG. 25 is a cross section of the plate of FIG. 24 taken along line 25-25.
Figure 26:
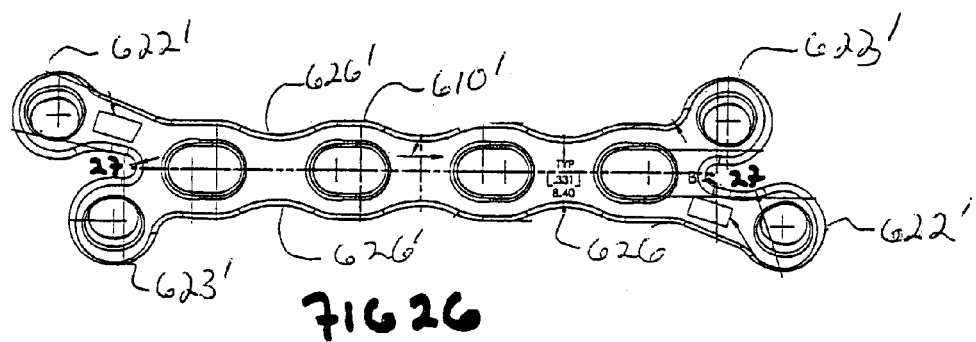
FIG. 26 is a top view of the beta version of the sixth embodiment of the plate in accordance with the invention.
Figure 27:
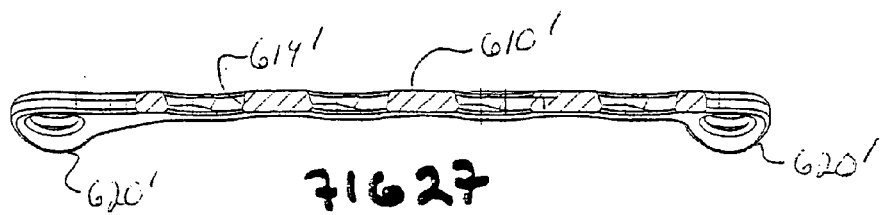
FIG. 27 is a cross section of the plate of FIG. 26 taken along line 27-27.

FIG. 9 is a second embodiment of a plate in accordance with the present invention which is intended to provide greater stability in indications, such as use in the spine, or pelvis. This plate 110 shares the same features as the design show in FIG. 1, but is somewhat more robust, with less tapering in the waist areas 126 of the trunk portion 112. The plate includes opposing pairs of asymmetrical arms, 120, which can again be viewed as diagonal pairs 122, 123 of arms, each including a set of screw holes 124. The trunk area 112 further includes slotted screw holes 114 which can be similarly used to cause a compression between them. The bottom side is radiused as for the small bone area, but with a gentler curvature of radius.

FIG. 10 is a beta version of the plate shown in FIG. 1. Thus, it is a mirror image of the plate, with corresponding elements such as a trunk portion 12', a pair of angled arms 20' at either end each having a screw hole 24', and the trunk portion 12' having two compression slots 14' that can be used to apply a compressive force in the direction indicated by the arrow 17' by placing the screw near the front of the slot, or can be used at a neutral compression by placing the screw in the middle of the slot when they are first put in. FIG. 11 is a cross-section of the plate of FIG. 10.

FIGS. 12 through 14 illustrate an embodiment of the plate 310,310' with a shorter trunk 312,312' that serves principally to join the two ends bearing the arms 320,320' and including a single narrowed waist area 326,326'. The arms 320,320' each include screw holes 324,324' which are rounded and provide the option of conical multi-axis fixation as shown and described for the first embodiment. FIGS. 16 through 19 illustrate an embodiment of a plate 410,410' having two opposing pairs of arms 420, 420' each including the multi-axis screw hole 424 and having a relatively short trunk portion 412, 412' having a single compression slot 414, 414'. FIGS. 20 through 23 illustrate both the alpha and beta version of an embodiment of the plate 510, 510' which have the pairs of asymmetrical arms 520, 520' and including a central trunk area 512, 512' with three compression slots 514,514' separated by narrowed waist areas 526, 526'. FIGS. 24 through 27 illustrate both the alpha and beta version of an embodiment of the plate 610, 610' which have the corresponding diagonally opposing arms 622 and 623, and 622', and 623' and including a central trunk area 612, 612' with four compression slots 614, 614' separated by narrowed waist areas 526, 526'. FIGS. 28 through 31 illustrate an alpha and beta version of the plate 710, 710' having only a single pair of arms 720, 720' and a trunk portion 712, 712' optionally having one or more compression slots 714, 714'.

While in accordance with the patent statutes, the best mode and preferred embodiment have been set forth, the scope of the invention is not limited thereto, but rather by the scope of the attached claims.

What is claimed is:

1. A surgical plate system capable of being used to stabilize a small bone fracture comprising
   a Y-shaped plate that has an inferior surface and which has a concentric superior surface forming a portion of a cylinder, the plate consisting of a trunk and a pair of a first arm and a second arm,
   the trunk having a linear medial longitudinal axis along the superior surface extending between a first and a second end, and the inferior surface of the plate defining a curve transverse to the medial axis,
   the first arm and the second arm extending from the first end of the trunk, the inferior surface of the first arm and of the second arm following the same curve as the inferior surface of the trunk,
   the first arm having an ear with at least one screw hole defining a first screw axis perpendicular to a tangent to the top surface of the first ear, the first ear being attached to the trunk by a linking section having a waist, a first angle and a first length being defined by a line from the center of the first arm screw hole to the intersection of the medial longitudinal axis of the trunk, and,
   the second arm having a second ear with at least one second screw hole defining a second screw axis perpendicular to a tangent to the top surface of the second ear, the second ear being attached to the trunk by a linking section having a waist, a second angle and a second length being defined by a line from the center of the second arm screw hole to the intersection of the medial longitudinal axis of the trunk, and
   the first angle and the first length being different from the second angle and the second length whereby the first screw axis and the second screw axis converge toward the inferior side of the plate but do not intersect.

2. A surgical plate system as set forth in claim 1 wherein the curve is constant along the medial axis.

3. A surgical plate system as set forth in claim 2 wherein the curve is a portion of a circle and the plate defines a segment of a cylinder.

4. A surgical plate system as set forth in claim 1 wherein the waist of the linking section of the first arm and of the second arm is configured to bend relative to the trunk section in response to a force applied before or during surgery without deforming the screw hole.

5. A surgical plate system as set forth in claim 1 wherein the trunk has a through hole.

6. A surgical plate system as set forth in claim 5 wherein the trunk has at least two through holes and a waist area between the through holes which encourages bending of the waist area in response to a force applied before or during surgery.

7. A surgical plate system as set forth in claim 1 wherein the trunk has a compression slot.

8. A surgical plate system as set forth in claim 7 wherein the compression slot comprises a slot having an internal edge which includes a shoulder that slopes toward the inferior side of the plate as it extends away from the first end of the trunk.

9. A surgical plate system as set forth in claim 7 wherein the superior surface of the trunk includes a visual indication of the direction in which the compression slot can be used to apply compression.

10. A surgical plate system as set forth in claim 1 further including screws having a threaded shafts and a head wherein the screw holes and the screw heads have a mating interface such that the screws can engage the screw hole so as to allow a plurality of angular orientations of the screw axis 11. An implant system capable of being used to stabilize a small bone fracture comprising
a pre-contoured plate which is a Y-shaped plate, the plate consisting of a trunk defining a medial longitudinal axis with a first end and an opposing second end, and a first arm and a second arm extending from the first end of the trunk,
the trunk having a continuous radial curve in the z direction about the longitudinal axis and the first arm and the second arm following the radial curve of the trunk so as to spiral about the longitudinal axis toward each other,
the first arm having an ear with at least one screw hole defining a first screw axis, the first ear being attached to the trunk by a linking section having a waist, a first angle and a first length being defined by a line from the center of the first arm screw hole to the intersection of the longitudinal axis of the trunk, and the linking section waist being configured to bend relative to the trunk section without deforming the screw hole,
the second arm having a second ear with at least one second screw hole defining a second screw axis, the second ear being attached to the trunk by a linking section having a waist, a second angle and a second length being defined by a line from the center of the second arm screw hole to the intersection of the longitudinal axis of the trunk, the linking section waist being configured to bend relative to the trunk section without deforming the through hole, and
the first angle being different from the second angle by from about 2° to about 20° and the first length being different from the second length whereby the first screw axis and the second screw axis converge toward the inferior side of the plate but do not intersect.

12. An implant system as set forth in claim 11 wherein the radial curve is constant along the longitudinal axis.

13. An implant system as set forth in claim 12 wherein the plate defines a segment of a cylinder.

14. An implant system as set forth in claim 13 wherein the trunk has at least two through holes and a waist area between the through holes which encourages bending of the waist area in response to a force applied before or during surgery.

15. An implant system as set forth in claim 11 wherein the trunk has a through hole.

16. An implant system as set forth in claim 11 wherein the trunk has a compression slot.

17. An implant system as set forth in claim 16 wherein the compression slot comprises a slot having an internal edge which includes a shoulder that slopes toward the inferior side of the plate as it extends away from the first end of the trunk.

18. An implant system as set forth in claim 16 wherein the superior surface of the trunk includes a visual indication of the direction in which the compression slot can be used to apply compression.

19. An implant system as set forth in claim 11 further including screws having a threaded shafts and a head wherein the screw holes and the screw heads have a mating interface such that the screws can engage the screw hole so as to allow a plurality of angular orientations of the screw axis.

* * * * *